US00PP15732P2

(12) United States Plant Patent
Thomsen

(10) Patent No.: US PP15,732 P2
(45) Date of Patent: Apr. 26, 2005

(54) ***EUPHORBIA MILII* PLANT NAMED 'RHEA'**

(50) Latin Name: *Euphorbia milii*
Varietal Denomination: Rhea

(75) Inventor: Steen Thomsen, Hjortebjerg (DK)

(73) Assignee: Gartneriet Hjortebjerg I/S (DK)

( * ) Notice: Subject to any disclaimer, the term of this patent is extended or adjusted under 35 U.S.C. 154(b) by 0 days.

(21) Appl. No.: 10/799,692

(22) Filed: Mar. 15, 2004

(30) Foreign Application Priority Data

May 28, 2003 (QZ) ..... PBR 2003/1009

(51) Int. Cl.[7] ..... A01H 5/00
(52) U.S. Cl. ..... Plt./302

(58) Field of Search ..... Plt./302

(56) References Cited

PUBLICATIONS

UPOV ROM GTITM computer database 2004/02 citations for 'Rhea'.*

* cited by examiner

*Primary Examiner*—Bruce R. Campell
*Assistant Examiner*—W C Haas
(74) *Attorney, Agent, or Firm*—Foley & Lardner, LLP

(57) ABSTRACT

A new distinct cultivar of *Euphorbia milii* plant named 'Rhea', characterized by its pink floral bract color from R.H.S. 69C to R.H.S. 68A; very dense and bushy plant form; vigorous but limited growth habit and small flowers on thick yellow-green peduncles R.H.S. 195A.

3 Drawing Sheets

Latin name of the genus and species of the plant claimed: *Euphorbia milii* Desmoul.
Variety denomination: 'Rhea'.

BACKGROUND OF THE INVENTION

The present Invention relates to a new and distinct cultivar of *Euphorbia milii* plant, botanically known as *Euphorbia milii* Desmoul, commonly known by the name Crown of Thorns, and hereinafter referred to by the name 'Rhea'.

The new *Euphorbia milii* is a product of a planned breeding program conducted by the Inventor, Steen Thomsen, in Haarslev, Fyn, Denmark. The new *Euphorbia milii* originated from a cross made in 2001 by the Inventor with unnamed cultivars of *Euphorbia milii* Desmoul. The male and female parental cultivars are unnamed, unpatented seedlings of *Euphorbia milii* Desmoul. The Inventor selected the new *Euphorbia milii* cultivar as a single plant from the progeny of the above crossing in 2001 on the basis of flower and compact, freely branching habit. Plants of the new *Euphorbia milii* are upright, compact and have a unique color and abundant, small flowers.

Asexual reproduction of the new cultivar by terminal cuttings taken and propagated and trial production batches in Denmark, has shown that the unique features of this new *Euphorbia milii* are stable and reproduced true to type in many successive generations.

BRIEF SUMMARY OF THE INVENTION

The following traits have been repeatedly observed and are determined to be the unique characteristics of 'Rhea'. These characteristics in combination distinguish 'Rhea' as a new and distinct cultivar:

1. Pink floral bract color from R.H.S. 69C to R.H.S. 68A.
2. Very dense and bushy plant form.
3. Vigorous but limited growth habit.

4. Small flowers on thick yellow-green peduncles R.H.S. 195A.

Plants of the cultivar 'Rhea' can be compared to plants of the cultivar *Euphorbia milii* 'Themis' (unpatented). In side-by-side comparisons conducted by the Inventor in Haarslev, Denmark, plants of the cultivar 'Rhea' and the cultivar 'Themis' differ in the following characteristics:

1. Plants of the new *Euphorbia milii* have pink colored bracts and staminate cyathia with yellow green-margined glands.
2. Plants of the new *Euphorbia milii* have smaller dark green leaves than 'Themis'.
3. Plants of the new *Euphorbia milii* have shorter and stiffer peduncles than plants of the cultivar 'Themis'.
4. Plants of the new *Euphorbia milii* are more compact than the plants of the cultivar 'Themis'.

Plants of the cultivar 'Rhea' have not been observed under all possible environmental conditions. The phenotype may vary somewhat with variations in environment such as temperature, light intensity, day length, and fertility level without, however, any variance in genotype.

BRIEF DESCRIPTION OF THE PHOTOGRAPHS

The accompanying color photographs illustrate the overall appearance and details of flower form, color and structures of the new cultivar, showing the colors as true as it is reasonably possible to obtain in colored reproductions of this type. Colors in the photographs may differ slightly from the color values cited in the detailed botanical description, which more accurately describe the actual colors of the new *Euphorbia milii.*

The first photograph shows a side view of a typical flowering plant of 'Rhea', as grown in an 11 cm pot.

The second photograph shows a top view of the flowering plant of 'Rhea'.

The third photograph is a close-up of the young and older floral cymes of 'Rhea'.

DETAILED BOTANICAL DESCRIPTION

In the following description, color references are made to The Royal Horticultural Society Colour Chart, $4^{th}$ edition, where general terms of ordinary dictionary significance are used. Plants were grown under greenhouse conditions.

Plants used for this description were grown for about 16 weeks after cutting and produced in 11 cm pots. Other pot sizes can be used and the plants are intended for indoor use or as a bedding plant in temperate climates although it is a perennial garden plant in tropical and subtropical areas.

Botanical classification: *Euphorbia milii* Desmoul cultivar 'Rhea'. Euphorbiaceae, Spurge family.

Parentage:

*Female parent.*—Unnamed seedling plant of *Euphorbia milii.*

*Male parent.*—Unnamed seedling plant of *Euphorbia milii.*

Propagation:

*Type cutting.*—Terminal vegetative cuttings taken from plants kept in the vegetative stage by shading and high temperatures (25C).

*Time to initiate roots.*—About 10 to 14 days at 18 to 21 C in tunnels in a greenhouse.

*Root description.*—Fine, well branched.

Plant description:

*Form.*—Perennial plant with upright plant habit. *Euphorbia milii* 'Rhea' flowers in cymes with cyathia subtended by colored bracts. Freely branching with about 8 lateral flowering branches forming at every node; dense and bushy. Stems are square to pentagonal with ridges about 10 mm thick at the base. By each node appear groups of thorns: 1 large 7 mm and 2 smaller 3 mm. Young thorns are yellow-green: 151A; while the older ones becomes stiffer and changes color to gray-brown (197B).

*Crop time.*—After rooting, about 16 weeks are required to produce finished flowering plants in 11 cm pots.

*Plant height* (*soil level to top of plant plane*).—About 8 cm. Width: 12 cm.

*Vigor.*—Vigorous growth rate.

Foliage description: Leaves alternate, single, obovate, entire.

*Size.*—Length: 5 cm. Width: About 30 mm.

*Apex.*—Acute.

*Base.*—Cuneate to almost decussate.

*Texture.*—Smooth, waxy, dull, glabrous.

*Color.*—Young foliage, upper and lower surfaces: 146C and N144D, yellow-green. Mature foliage, upper and lower surfaces: 137A and 147C respectively. Venation, 137C.

Flower description:

*Flower arrangement and shape.*—Floral arrangements composed of cymes. The flowers (cyathia) are starkly reduced so only a gland and the reproductive organs are present. Subtending the cyathia are two colored bracts. The flowers are further complicated by the unique feature of funnel shaped floral buds appearing at the base of the bracts in two or more layers.

*Natural flowering season.*—Continuous throughout the spring and summer in subtropical and tropical regions. In colder climates season can be extended by greenhouse production with high temperatures and supplementary irradiance.

*Flower longevity on the plant.*—5 to 9 weeks, longevity of individual flowers is highly dependent on temperature and light conditions. Bracts turn green with age. Entire cymes drop after withering.

*Inflorescence size.*—Diameter: About 3–4 cm, height: 7 cm.

*Flowers.*—3 mm diameter, Bracts: overlapping at base, ovoid to inverted cordate, approximately 10 mm in length by 12 mm in width, pink color from 69A, to 68A (red-purple group).

*Glands.*—5 from 29A shiny orange to 151B yellow-green during development.

*Anthers.*—Appear after flowers mature; stamen color 71B, red-purple and pollen color 5A, yellow.

*Pistil and stigma.*—Appear before cyathia mature; color 70AC, red-purple.

*Peduncle.*—Strength: soft. Length: About 5 cm. Diameter: About 3 mm. Color: 146C, green at an angle of 30°.

*Pedicels.*—5 cm long, 2 mm thick strong color: 146C, yellow-green.

Weather tolerance: Plants of the new *Euphorbia milii* have exhibited good tolerance to draught, rain and wind, however flowering may cease during cold and dark periods (<15C).

Pest tolerance: Plants of the new *Euphorbia milii* have exhibited good tolerance to following fungi: Mildew, and Thivaliopis. Also, they appear to be less infected by Thrips (Franklinellea).

I claim:

1. A new and distinct cultivar of *Euphorbia milii* plant named 'Rhea', as illustrated and described herein.

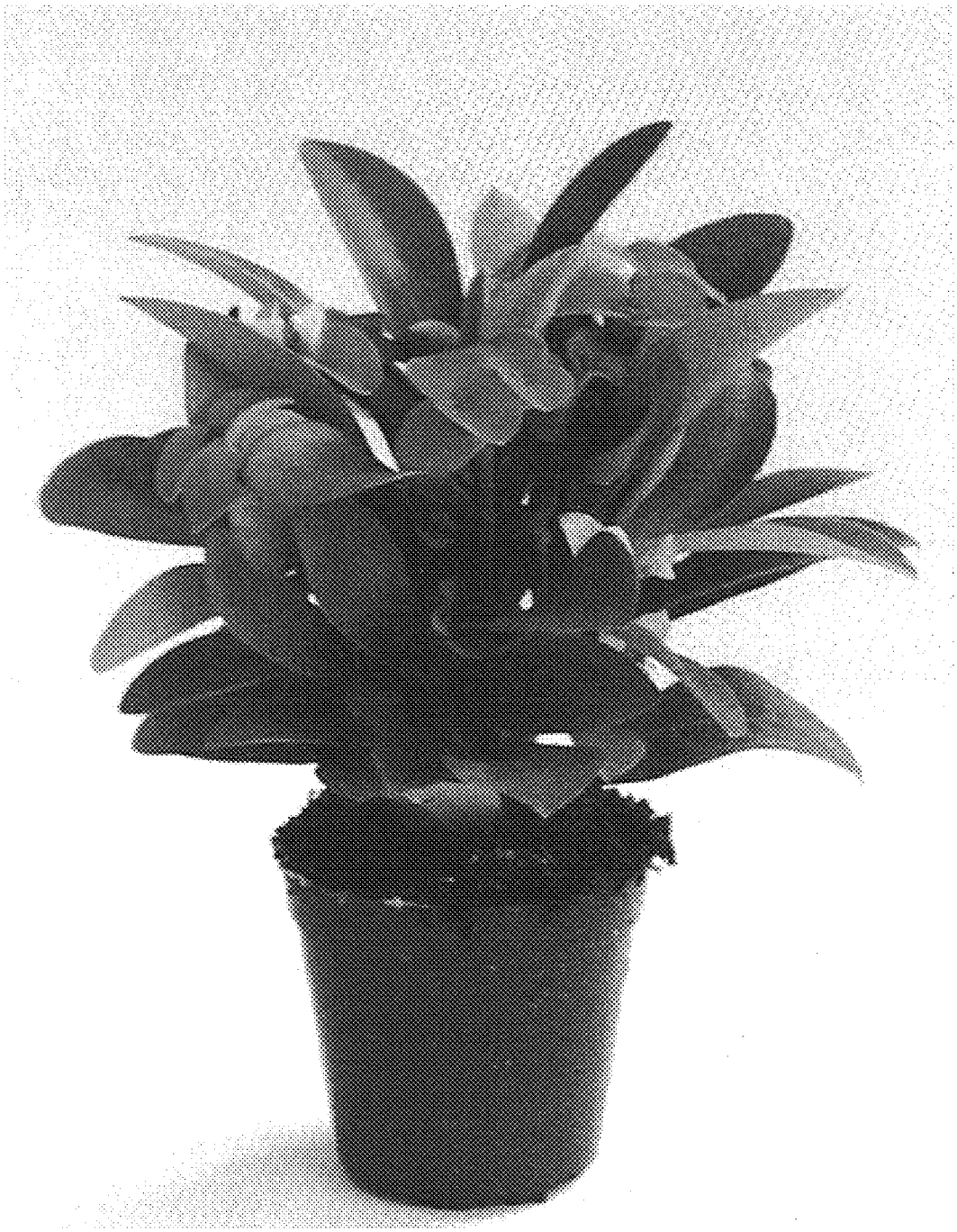

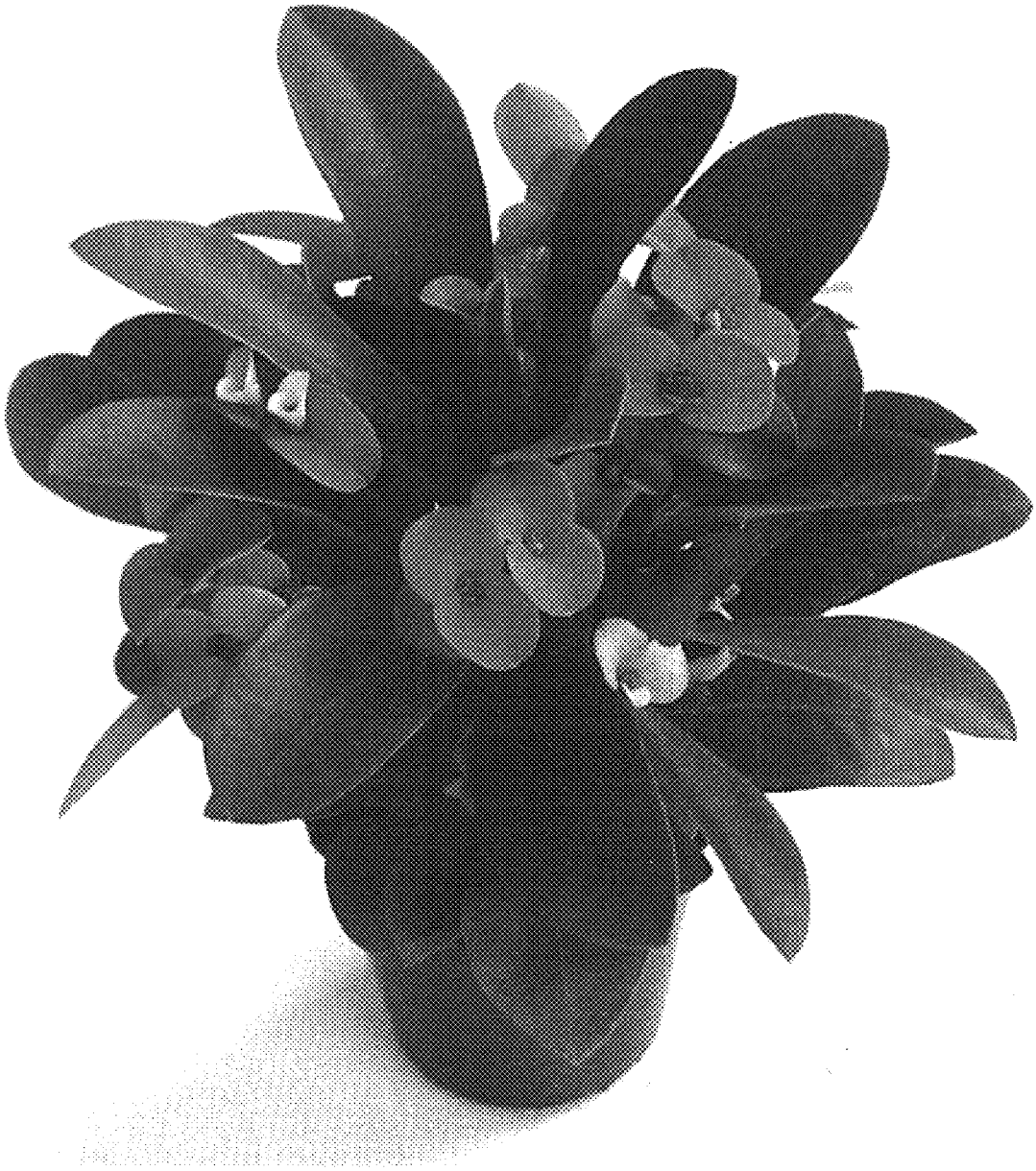

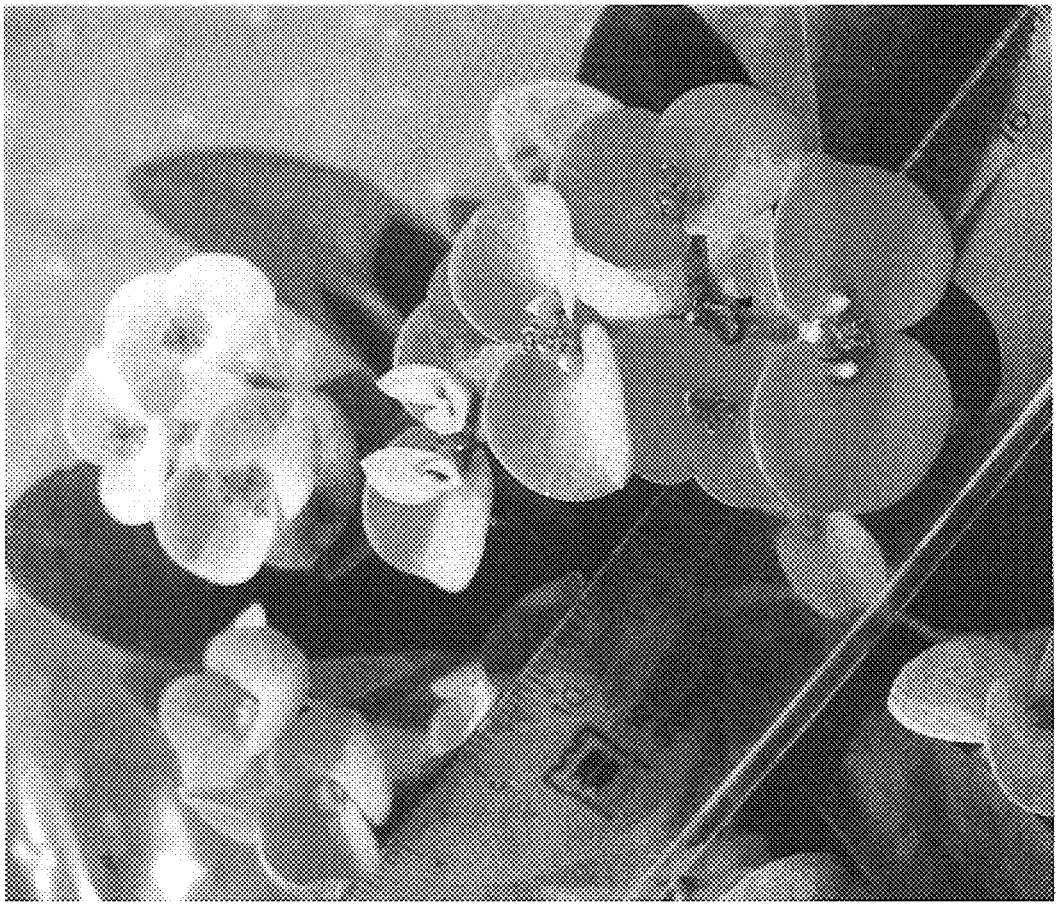

* * * * *